US008855955B2

(12) United States Patent
Peyvan et al.

(10) Patent No.: US 8,855,955 B2
(45) Date of Patent: Oct. 7, 2014

(54) PROCESS AND APPARATUS FOR MEASURING BINDING EVENTS ON A MICROARRAY OF ELECTRODES

(75) Inventors: Kia Peyvan, Seattle, WA (US); Michael Bizak, Kirkland, WA (US); Colin Campbell, Seattle, WA (US); Rand William Lee, Kirkland, WA (US)

(73) Assignee: Custom Array, Inc., Bothwell, WA (US)

( * ) Notice: Subject to any disclaimer, the term of this patent is extended or adjusted under 35 U.S.C. 154(b) by 631 days.

(21) Appl. No.: 11/238,470

(22) Filed: Sep. 29, 2005

(65) Prior Publication Data

US 2007/0072169 A1   Mar. 29, 2007

(51) Int. Cl.
   *G01R 19/00*   (2006.01)
(52) U.S. Cl.
   CPC ................. *G01R 19/0092* (2013.01)
   USPC ........................................... 702/64
(58) Field of Classification Search
   CPC ................................. G01R 19/0092
   USPC ........................................... 702/64
   See application file for complete search history.

(56) References Cited

U.S. PATENT DOCUMENTS

| 3,950,357 | A |   | 4/1976  | Kahan et al.       |         |
|-----------|---|---|---------|--------------------|---------|
| 4,165,320 | A |   | 8/1979  | Ondetti et al.     |         |
| 4,563,263 | A |   | 1/1986  | Oyama et al.       |         |
| 4,713,347 | A | * | 12/1987 | Mitchell et al.    | 436/501 |
| 4,840,893 | A |   | 6/1989  | Hill et al.        |         |
| 5,143,854 | A |   | 9/1992  | Pirrung et al.     |         |
| 5,445,934 | A |   | 8/1995  | Fodor et al.       |         |
| 5,540,828 | A |   | 7/1996  | Yacynych           |         |
| 5,653,939 | A |   | 8/1997  | Hollis et al.      |         |
| 5,667,667 | A |   | 9/1997  | Southern           |         |
| 5,759,371 | A | * | 6/1998  | Walker et al.      | 204/474 |
| 5,912,339 | A |   | 6/1999  | Miller et al.      |         |
| 5,929,208 | A |   | 7/1999  | Heller et al.      |         |
| 5,953,681 | A | * | 9/1999  | Cantatore et al.   | 702/31  |
| 6,021,347 | A | * | 2/2000  | Herbst et al.      | 607/2   |
| 6,051,380 | A |   | 4/2000  | Sosnowski          |         |
| 6,093,302 | A | * | 7/2000  | Montgomery         | 205/122 |
| 6,280,595 | B1|   | 8/2001  | Montgomery         |         |
| 6,444,111 | B1|   | 9/2002  | Montgomery         |         |

(Continued)

FOREIGN PATENT DOCUMENTS

| JP | 2006-166601 | * | 6/2005 |
| JP | 2005166601  |   | 6/2006 |

(Continued)

OTHER PUBLICATIONS

English Abstract of JP 2006-166601, Jun. 2005.*

(Continued)

*Primary Examiner* — Michael Nghiem
(74) *Attorney, Agent, or Firm* — Sci-Law Strategies, PC

(57) ABSTRACT

There is disclosed a process and apparatus for reading electrical current of electrodes on a microarray of electrodes. Those electrodes having binding events are detected by a difference in electrical current flow. Enzymes on targets catalyze the conversion of substrate to product, which is detectable by electrochemical reduction at each electrode on the microarray of electrodes. The apparatus has an integration circuit that provides a voltage output that is measured and recorded over time and used to calculate an average current flow. A potentiometer equalizes voltage at electrodes undergoing measurement compared to grounded electrodes.

27 Claims, 3 Drawing Sheets

(56) References Cited

U.S. PATENT DOCUMENTS

| | | | |
|---|---|---|---|
| 6,456,942 | B1 | 9/2002 | Anderson et al. |
| 6,475,699 | B2 | 11/2002 | Uetani et al. |
| 6,518,024 | B2 | 2/2003 | Choong et al. |
| 6,576,426 | B2 | 6/2003 | Southern et al. |
| 6,743,564 | B2 | 6/2004 | Hatakeyama et al. |
| 6,780,582 | B1 | 8/2004 | Wagner et al. |
| 6,960,298 | B2 | 11/2005 | Krotz et al. |
| 7,008,769 | B1 | 3/2006 | Henderson et al. |
| 7,541,314 | B2 | 6/2009 | Suciu et al. |
| 7,597,789 | B2 * | 10/2009 | Harima .................. 204/406 |
| 2002/0063122 | A1 * | 5/2002 | Katzman et al. ............ 219/497 |
| 2002/0090738 | A1 | 7/2002 | Cozzette et al. |
| 2002/0172963 | A1 | 11/2002 | Kelley |
| 2003/0082601 | A1 * | 5/2003 | Dill .................................. 435/6 |
| 2003/0111356 | A1 | 6/2003 | Strathmann |
| 2003/0113713 | A1 | 6/2003 | Glezer |
| 2003/0134989 | A1 | 7/2003 | Aldrich et al. |
| 2004/0023258 | A1 * | 2/2004 | Patolsky et al. ................. 435/6 |
| 2004/0072158 | A1 * | 4/2004 | Henkens et al. ................ 435/6 |
| 2004/0073017 | A1 | 4/2004 | Skrzypcznski et al. |
| 2005/0043894 | A1 * | 2/2005 | Fernandez ..................... 702/19 |
| 2005/0212902 | A1 * | 9/2005 | Cook et al. ................... 347/248 |
| 2005/0239112 | A1 | 10/2005 | Padmanabhan |
| 2005/0272088 | A1 | 12/2005 | Cook |
| 2006/0101471 | A1 | 5/2006 | Adermann |
| 2006/0102471 | A1 * | 5/2006 | Maurer et al. ........... 204/290.01 |
| 2006/0160100 | A1 | 7/2006 | Gao et al. |
| 2006/0231411 | A1 * | 10/2006 | Maurer et al. ................. 205/413 |
| 2007/0231794 | A1 * | 10/2007 | Dill et al. ........................... 435/6 |
| 2007/0292855 | A1 | 12/2007 | Dubin |
| 2008/0035494 | A1 * | 2/2008 | Gomez et al. ................ 205/792 |

FOREIGN PATENT DOCUMENTS

| | | | |
|---|---|---|---|
| WO | WO9603417 | | 2/1996 |
| WO | WO0051721 | | 9/2000 |
| WO | WO 03/019147 | * | 3/2003 |
| WO | WO03020415 | | 3/2003 |

OTHER PUBLICATIONS

Patolsky, et al. "Highly Sensitive Amplified Electronic Detection . . . " Chem. Eur. J., 2003, 1137-1145, vol. 9, No. 5 Wiley-VCH Weinheim.
Wang, Joseph "Survey and Summary from DNA Biosensors . . . " Nucleic Acids Research 2000, 3011-3016, vol. 28, No. 16 Oxford University Press.
Drummond, et al., "Electrochemical DNA Sensors" Nature Biotechnology Oct. 2003, 1192-1199, vol. 21, No. 10 Nature Publishing Group.
Ghindilis, et al., "Immunosensors: Electrochemical Sensing and Other . . . " Biosensors & Bioelectronics 1998, 113-131 vol. 13, No. 1 Elsevier Sciences S.A.
Campbell, et al., "Enzyme-Amplified Amperometric Sandwich Test for RNA and DNA" Anal. Chem., 2002, 158-162, 74(1) American Chemical Society.
Dill, et al., "Immunoassays and Sequence-Specific DNA Detection on a Microchip . . . " J. Biochem. Biophys. Methods 2004, 59 181-187, Elsevier B.V.
Wang, et al., "Dual Enzyme Electrochemical Coding for Detecting DNA Hybridization" Analyst 2002 vol. 1279-1282, The Royal Society of Chemistry.
Rossier, et al., "Enzyme Linked Immunsorbent Assay on a Microchip . . . " Lab on a Chip 2001, vol. 1, 153-157, The Royal Society of Chemistry.
Patolsky, et al., "Enzyme-Linked Amplified Electrochemical Sensing . . . " Langmuir 1999, 3703-3706, vol. 15, No. 11, American Chemical Society.
Ashfari et al., "Application of Complementary DNA Microarray Technology to Carcinogen Identification, Toxicology, and Drug Safety Evaluation" Cancer Res. 59:4759, (1999).

Bard et al., "Azo, Azoxy and Diazo Compounds," Encyclo. of Electrochemistry of the Elements, 1979, pp. 179-209, vol. XIII-4, NY.
Beier et al., "Versatile Derivatisation of Solid Support Media for Convalent Bonding . . . " Nucleic Acids Research, 1999, pp. 1970-1977, vol. 27, No. 9.
Cahill and Nordhoff, "Protein Arrays & Their Role in Protemics" Adv. Biochem. Engin/Biotechnol., 2003, pp. 177-187, vol. 83.
Campbell et al., "Enzyme-Amplified Amperometric Sandwich Test for RNA and DNA" Anal. Chem., 2002, 158-162, 74(1) American Chemical Society.
Dill et al., "Antigen Detection Using Microelectrode Array Microchips" Analytica Chimica Acta, 2001, pp. 69-78, vol. 444.
Dill et al., "Immunoassays and Sequence-Specific DNA Detection on a Microchip . . . " J. Biochem. Biophys. Methods, 2004, 59 pp. 181-187, Elsevier B.V.
Drummond et al., "Electrochemical DNA Sensors" Nature Biotechnology Oct. 2003, 1192-1199, vol. 21, No. 10 Nature Publishing Group.
Egeland et al., "An Electrochemical Redox Couple Activitated by Microelectrodes for Confined Chemical Patterning of Surfaces" Analytical Chemistry (2002) vol. 74, pp. 1590-1596.
Fledler et al., "Diffusional Electrotitration: Generation of pH Gradients . . . " Analytical Chemistry, Mar. 1. 1995, pp. 820-828, vol. 67, No. 5.
Fodor et al., "Light-Directed, Spatially Addressable Parallel Chemical Synthesis" Science, Feb. 15, 1991, 767-773, vol. 251.
Gao et al., "In Situ Synthesis of Oligonucleotide Microarrays" Biopolymers Mar. 2004, pp. 579-596, vol. 73.
Ghindilis et al., "Immunosensors: Electrochemical Sensing and Other . . . " Biosensors & Bioelectronics 1998, pp. 113-131, vol. 13, No. 1, Elsevier Sciences S.A.
Greene et al., "Protective Groups in Organic Synthesis" Third Edition, Wiley-Interscience, 1999.
Guo, et al., "Direct Fluorescence Analysis of Genetic Polymorphisms by Hybridization with Oligonucleotide . . . " Nucl. Acids Res., 1994, pp. 5456-5465, vol. 22, No. 24.
Hacia "Resequencing and mutational analysis using oligonucleotide microarrays" Nature Genetics 21 Supp.: 42, (1999).
Hacia et al., "Applications of DNA Chips for Genomic Analysis" Mol. Psychiatry, Nov. 1998, pp. 483-492, vol. 3, No. 6.
Hammerich et al., "Organic Electrochemistry, an Introduction & Guide" ed. By Lund and Baizer, 3rd Edition, 1991 pp. 615-657 Marcel Dekker, Inc., NY.
Johnston, "Gene Chips: Array of Hope for Understanding Gene Regulation" Curr. Biology, Feb. 26, 1998, R171-R174, vol. 8.
Krotz et al., "Large-Scale Synthesis of Antisense Oligonucleotides Without Chlorinated Solvents" Organic Process Res & Dev, 2000, pp. 190-193, vol. 4.
Kurian et al., "DNA Chip Technology" J. Pathology, 1999, pp. 267-271, vol. 187.
Lane et al., "Electrochemistry of Chemisorbed Molecules . . . " J. Physical Chemistry, 1973, pp. 1411-1421, vol. 77, No. 11.
Leproust et al., "Characterization of Oligodeoxyribonucleotide Synthesis on Glass Plates" Nucl. Acids Res., 2001, pp. 2171-2180, vol. 29, No. 10.
Maskos and Southern, "Oligodeoxyribonucleotide Synthesis on Glass Plates", Nucl. Acids Res., 1992, pp. 1679-1684, vol. 20.
Moller et al.. "Anodic oxidation of cyclohexene: Dependence of the product distribution on the reaction variables" Electrochimica Acta, vol. 42, No. 13, Jan. 1, 1997, pp. 1971-1978.
Ono et al., "Nucleosides and Nucleotides. 121. Synthesis of Oligonucleotides . . . " Bioconjugate Chem. 1993, pp. 499-508, vol. 4.
Patolsky et al. "Highly Sensitive Amplified Electronic Detection of DNA . . . " Chem. Eur. J., 2003, pp. 1137-1145, vol. 9, No. 5 Wiley-VCH Weinheim.
Patolsky et al., "Enzyme-Linked Amplified Electrochemical Sensing . . . " Langmuir 1999, vol. 15, No. 1,1 pp. 3703-3706, Am. Chemical Society.
Paul et al., "Acid Binding and Detrytylation During Oligonucleotide Synthesis" Nucleic Acids Research, 1996, 3048-3052, vol. 24, No. 15.

(56) References Cited

OTHER PUBLICATIONS

Pellois et al., "Peptide Synthesis Based on t-Boc Chemistry & Solution Photogenerated Acids" J. Comb. Chem. 2000, pp. 355-360, vol. 2, No. 4.

Pillai, "Photoremovable Protecting Groups in Organic Chemistry" Synthesis 1980, pp. 1-26, vol. 39.

Ronlan, A. and Parker, V. D., "Anodic oxidation of phenolic compounds. Part II. Products and mechanisms of the anodic oxidation of hindered phenols" J. Chem. Soc. (C), 1971, pp. 3214-3218.

Rossier et al., "Enzyme Linked Immunsorbent Assay on a Microchip . . . " Lab on a Chip 2001, vol. 1, pp. 153-157, The Royal Society of Chemistry.

Septak, M. "Kinetic Studies on Depurination and Detritylation of CPG-bound Intermediates . . . " Nucleic Acids Research, 1996, pp. 3053-3058, vol. 24, No. 15.

Shchepinov et al., "Steric Factors Influencing Hybridisation of Nucleic Acids to Oligonucleotide Arrays" Nucl., Acids Res., 1997, pp. 115-1161, vol. 25, No. 6.

Shchepinov, M.S., "Oligonucleotide Dendrimers: From Poly-Labeled DNAc617 Probes to Stable Nano-Structures" Glen Report, Dec. 1999, vol. 12, No. 1.

Soriaga et al., "Determination of Orientation of Adsorbed Molecules . . . ", J. Am. Chem. Soc., 1982, pp. 3937-3945, vol. 104.

Wang, G. et al., "Synthesis of Oligonucleotides Containing . . . " Tetrahedron Letters, 1993, 6721-6724, vol. 34, No. 42, Great Britain.

Wang et al., "Dual Enzyme Electrochemical Coding for Detecting DNA Hybridization" Analyst 2002, 1279-1282, The Royal Society of Chemistry.

Wang, Joseph "Survey and Summary from DNA Biosensors . . . " Nucleic Acids Research 2000, pp. 3011-3016, vol. 28, No. 16 Oxford University Press.

Wilgenbus and Lichter, "DNA Chip Technology Ante Portas" J. Mol. Med., Nov. 1999, pp. 761-768, vol. 77.

Xie et al., Amperometric Detection of Nucleic Acid at Femtomolar Levels with a Nucleic Acid/Electrochemical Activator Bilayer on Gold Electrodes, 2004, vol. 76, pp. 1611-1617.

* cited by examiner

An example immunoassay sandwich having horseradish peroxidase enzyme

An example immunoassay sandwich having laccase enzyme

ELECTRODE SWITCHING

Measured Electrode $E_0$

Measured Electrode $E_1$

Measured Electrode $E_2$

PROCESS AND APPARATUS FOR MEASURING BINDING EVENTS ON A MICROARRAY OF ELECTRODES

TECHNICAL FIELD OF THE INVENTION

This invention provides a process and an apparatus for electrochemical detection on a microarray of electrodes. More specifically, the process and apparatus are useful for reading the electrical signal of each electrode by sequentially reading a set of electrodes. The electrodes utilize an enzyme-amplified redox chemistry that produces an electron proximate to an electrode when a binding event has occurred between a probe molecule on the microarray and a target molecule in a test sample added to the microarray.

BACKGROUND OF THE INVENTION

Microarray preparation methods for synthetic oligomers, including oligonucleotides (oligos) include the following: (1) spotting a solution on a prepared flat or substantially planar surface using spotting robots; (2) in situ synthesis by printing reagents via ink jet or other computer printing technology and using standard phosphoramidite chemistry; (3) in situ parallel synthesis using electrochemically generated acid for removal of protecting groups and using standard phosphoramidite chemistry; (4) in situ synthesis using maskless photo-generated acid for removal of protecting groups and using regular phosphoramidite chemistry; (5) mask-directed in situ parallel synthesis using photo-cleavage of photolabile protecting groups (PLPG) and standard phosphoramidite chemistry; (6) maskless in situ parallel synthesis using PLPG and digital photolithography and standard phosphoramidite chemistry; and (7) electric field attraction/repulsion for depositing fully formed oligos onto known locations.

An electrode microarray for in situ oligo synthesis using electrochemical deblocking is disclosed in Montgomery U.S. Pat. Nos. 6,093,302; 6,280,595, and 6,444,111 (Montgomery I, II, and III respectively), all of which are incorporated by reference herein. Another and materially different electrode array (not a microarray) for in situ oligo synthesis on surfaces separate and apart from electrodes using electrochemical deblocking is disclosed in Southern U.S. Pat. No. 5,667,667, which is incorporated by reference herein. Photolithographic techniques for in situ oligo synthesis are disclosed in Fodor et al. U.S. Pat. No. 5,445,934 and the additional patents claiming priority thereto, all of which are incorporated by reference herein. Electric field attraction/repulsion microarrays are disclosed in Hollis et al. U.S. Pat. No. 5,653,939 and Heller et al. U.S. Pat. No. 5,929,208, both of which are incorporated by reference herein. A review of oligo microarray synthesis is provided by: Gao et al., *Biopolymers* 2004, 73:579.

For microarrays, a photon-based detection system (i.e., optical detection) is generally used to detect a binding event. Most commonly, microarray detection processes use fluorescent tags on the targets for transduction of a binding event on a microarray. Chemiluminescent systems are also used. The amount of binding is related to the amount of fluorescence measured. Alternatively, visible dyes or luminescent tags may be used. For example, for DNA hybridization, the tag is attached to target DNA sequences to detect hybridization to a probe oligonucleotide attached to a microarray. Depending upon the intensity of the signal from the tag, such microarrays may have to be read through laser confocal microscope-based system for microarrays configured in a monolayer (such as those microarrays made through high density spotting or photolithography techniques) or by a video-type camera (such as a CCD camera) for those microarrays having a three-dimensional matrix for each spot in high density formats.

An alternative to fluorescence has been optical detection of probe-target binding. In a so-called scanometric assay, targets are labeled with catalytic gold nanoparticles. After binding with the probe, a silver salt is added to the solution and metallic silver is deposited where the nanoparticles are bound. Detection is similar to optical photographic development and is recorded using either a digital scanner or photographic techniques. This technique does alleviate some of the technical demands of fluorescent detection but it is unclear how sensitive scanometric techniques will be at spot sizes relegated by current state of the art microarrays.

Generally, photon-based readers are expensive, relatively large and cumbersome, extremely heavy and unsuitable for field-based deployment, rely on sophisticated numerical algorithms, and must be accurately calibrated before use; thus, use of such readers is generally limited to a laboratory setting. In each instance of "reading" the signal from a microarray, there is often stray light or other noise signals that cause false or inaccurate readings. Moreover, distinguishing between shades of gray or barely perceptible signals as true positives or false positives is difficult. Finally, there may be quenching of the fluorescent signal and auto absorption of the signal by other labels within close proximity to the bound target. The additional complexity associated with using a photon-based reader imparts added variability. Therefore, there is a need in the art for improvements to the detection process for analyzing binding events on microarrays. The present invention was made to address this need to improve detection of binding events on an electrode microarray by basing detection on electrical properties rather than light properties of electrodes having binding events.

BRIEF SUMMARY OF THE INVENTION

The present invention provides a process for reading electrical current of electrodes on a microarray of electrodes comprising:

(a) providing a measurement system having a control system, an integration circuit, a microarray chamber, a plurality of voltage lines, digital circuitry, and analog circuitry, wherein the control system, the integration circuit, and the microarray chamber are in circuit communication, wherein the microarray chamber contains a microarray having a plurality of electrodes in circuit communication with the control system and the integration circuit, wherein the voltage lines are switchably connectable to each electrode by the control system, wherein a first voltage line connects the microarray to the integration circuit and connects the integration circuit to the control system, wherein a second voltage line is settable to ground, wherein a third voltage line is settable to a programmable fixed voltage, wherein the integration circuit has an integrating transimpedance amplifier having a positive input and a potentiometer circuit connected to the positive input, wherein the potentiometer circuit is adjusted using an adjusting method to maintain approximately identical voltage of electrodes having current measured and electrodes not having current measured;

(b) initializing measurement by setting a measurement set of the electrodes to approximately ground using the second voltage line, setting a counter electrode voltage of at least one counter electrode using the third voltage line, and pausing for a steady state period, wherein the at least one counter electrode is in fluid communication with the measurement set of the electrodes;

(c) measuring current for each electrode of the measurement set of electrodes current by (i) connecting a measurement electrode to the integration circuit having a reset switch closed using the first voltage line, (ii) pausing for an electrode settling period, (iii) opening the reset switch to measure and record a voltage response from the output of the integration circuit for a measurement time, (iv) closing the reset switch, and (v) switching the measurement electrode back to the second voltage line; and (d) calculating current of each of the electrodes of the measurement set by linear regression of the voltage response and time, wherein a slope is obtained, wherein the current is equal to negative of the slope multiplied by a capacitor value of the integration circuit capacitor.

Preferably, the adjusting method for the potentiometer circuit is selected from the group consisting of manual adjustment before assembling and software adjustment using computer software and a measurement and feedback circuit having a digital to analog converter and an analog to digital converter. Preferably, the electrode settling period is approximately 10 to 600 microseconds. Preferably, the set voltage of the at least one counter electrode is approximately 0.02 to 0.5 volts. Preferably, the steady state period is approximately 4 to 60 seconds. Preferably, the capacitor value is approximately 5 to 20 picofarads. Preferably, the measurement time is approximately 0.5 to 5 milliseconds. Preferably, the sampling rate is approximately one data pair every 10 to 100 microseconds.

Preferably, the counter electrode comprises electrodes on a perimeter part of the microarray, wherein the perimeter part includes three columns of electrodes on a long side of the microarray and five rows of electrodes on a short side of the microarray. Preferably, the microarray chamber has electromagnetic interference shielding. Preferably, the microarray chamber is shielded from light. Preferably, the integration circuit is shielded. Preferably, the digital circuitry is routed away from the analog circuitry.

In another embodiment, the present invention provides an apparatus for integrating voltage to measure current of electrodes on a microarray comprising:

(a) an electrical network having eight network terminals (A, B, C, D, E, F, G, H) including (i) an integrating transimpedance amplifier having a negative amp input connected to the network terminal (A), a positive amp input connected to the network terminal (B), and an amp output connected to the network terminal (C), (ii) an operational amplifier having a positive opamp input connected to the network terminal (D), a negative opamp input connected to the network terminal (B), and an opamp output connected to the network terminal (B), (iii) a programmable gain amplifier having gain G1 and a PGA input connected to the network terminal (C) and a PGA output connected to the network terminal (H), (iv) a first resistor having known resistance R1 connected between the network terminals (D) and (E), (v) a second resistor having known resistance R2 connected between the network terminal (D) and ground, (vi) a potentiometer having known resistance R3, a potentiometer output connected to the network terminal (E), and potentiometer inputs connected between the network terminals (F) and (G), (vii) a capacitor of known capacitance C1 connected between the network terminals (A) and (C), and (viii) a reset switch connected between the network terminals (A) and (C);

(b) a plurality of voltages lines having a measurement line, a ground line, and a counter electrode line, wherein the voltages lines are switchably connectable to electrodes on a microarray of electrodes held in a microarray chamber, wherein during measurement the measurement line is connected between network terminal (A) and a measurement electrode, the ground line is connected to a plurality of electrodes not being measured, and the counter electrode line is connected to at least one counter electrode;

(c) one or more external power sources, wherein the one or more external power sources provide a first source of potential across the network terminals (F) and (G), a second source of potential to power the operational amplifier, a third source of potential to power the integrating transimpedance amplifier, a fourth source of potential to power the programmable gain amplifier, and a fifth source of potential to power the reset switch; and (d) a computer control and data acquisition system having an input line connected to the network terminal (H) and in circuit communication with the integration circuit, the external power sources, and the voltage lines using analog circuitry and digital circuitry.

Preferably, the potentiometer is adjustable using a method selected from the group consisting of manual adjustment before assembling and software adjustment using computer software and a measurement and feedback circuit having a digital to analog converter and an analog to digital converter.

Preferably, the counter electrode line is adjustable to a voltage of approximately 0.02 to 0.5 volts. Preferably, C1 is approximately 10 picofarads. Preferably, the microarray chamber has electromagnetic interference shielding. Preferably, the microarray chamber is shielded from light. Preferably, the integration circuit is shielded. Preferably, the digital circuitry is separated from the analog circuitry. Preferably, R1 is approximately 49,900 ohms. Preferably, R2 is approximately 100 ohms. Preferably, R3 is approximately 10,000 ohms.

DETAILED DESCRIPTION OF THE INVENTION

Addressable Electrode Microarrays and Binding Events

Figure 1:
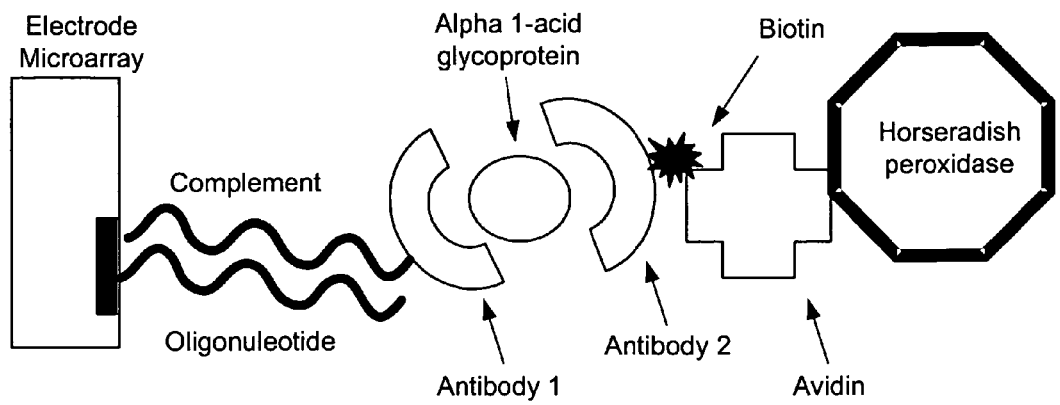
FIG. 1 illustrates a chemical reaction scheme when horseradish peroxidase (HRP) is used as an enzyme for detection of a binding event on a microarray. Specifically, the analyte (target) is alpha 1-acid glycoprotein (AGP). The analyte binding to the microarray is detected by first forming a complex with a second antibody that is labeled with biotin. The second antibody is specific for an epitope of AGP. An avidin-labeled HRP enzyme is then added, and the avidin attaches to the biotin. The microarray site used for detecting AGP as the analyte has another antibody binding to a different epitope on AGP as the probe. The first antibody (labeled "Antibody 1") is self-assembled to an oligonucleotide microarray through a tagged probe oligonucleotide. Products from HRP catalysis are reducible and hence detectable at an electrode on a microarray by making the electrode having the HRP bound thereto a cathode.

Electrode microarrays comprise a plurality of addressable electrodes. An addressable electrode is one where the electrode can be electronically controlled to create a current or voltage at the electrode. Electrode microarrays are preferably in a column and row format although other formats may be used. Electrodes may be circular or other suitable geometries including a partial annulus or a grid of lines suitably broken. Other geometries may be used including those disclosed in U.S. application Ser. No. 11/108,078, filed Apr. 15, 2005, entitled "Neutralization and Containment of Redox Species Produced by Circumferential Electrodes," which is incorporated by reference herein. Each electrode occupies a surface region of the microarray. Within a specific region having an electrode, molecules can be synthesized in situ. The types of molecules that may be synthesized include small molecules, oligomers, and polymers. Biomolecules such as peptides, DNA, and RNA may also be synthesized. Molecules synthesized on an electrode microarray are generally referred to as probes.

Electrode microarrays further and often have a porous reaction matrix (layer) attached to the microarray surface. The porous reaction matrix has probes attached to it and provides a three dimensional virtual flask for confinement of reagent at the electrode. The flask may be thought of as cylindrical in the case of a circular electrode. Preferably, the porous reaction matrix is selected from the group consisting of sucrose, monosaccharides, disaccharides, trisaccharides, polyethylene glycol, polyethylene glycol derivative, N-hydroxysuccinimide, succinimide derivatives, and combinations thereof. Other porous reaction matrix materials may be used including those disclosed in U.S. application Ser. No. 10/992,252, filed Nov. 18, 2004, entitled "Electrode Array device having an adsorbed porous reaction layer," which is incorporated by reference herein. Alternatively, the porous reaction layer is a membrane, wherein the membrane material is selected from the group consisting of polyvinyl alcohol, polyvinyl acetate, tricellulose acetate, polyurethane, agarose, controlled porosity glass with a PTFE resin, and combinations thereof.

Most commonly, a microarray contains a plurality of probe molecules. Alternatively and rarely, a microarray may have one probe molecule type. In the most common form of a microarray, the probes are oligonucleotides that can bind to a complementary sequence of DNA or RNA, wherein the DNA or RNA is a target oligonucleotide. Depending upon the hybridization conditions, a target having a region that is nearly complementary to a probe may bind to the probe. Detection of binding or hybridization events on a microarray is one of the main challenges in obtaining useful and accurate data. Most of the marketed products are generally made by spotting or ink-jet printing oligonucleotides onto planar, non-porous surfaces such as glass slides. There are sample-labeling kits commercially available that cause the sample oligonucleotide (target) to become labeled with a fluorescent dye. Often it is a fluorescent dye sold under the trademarks of TEXAS RED®, or CY® dyes including CY3 DIRECT® and CY5 DIRECT®. Most commonly, the microarray is "read" through a common fluorometer arrangement with either microscopic magnification or imaging stitching.

Reading involves looking for fluorescence at the known locations where the probe was spotted or synthesized. Reading fluorescence of a microarray to detect a binding event is the detection method universally used. However, there are optical issues, difficulty in labeling with fluorescent dyes, occasional high background problems, and most importantly, extremely high costs associated with fluorescent microscopic equipment. Therefore, there is a need to detect binding events on microarrays using lower cost equipment having less complexity while providing reduced variability.

The present inventive method and apparatus uses electrochemical detection of binding events to provide a lower cost detection method with less variability. The method and apparatus involves application of a voltage or current to electrodes on an electrode microarray to detect a binding event. The voltage or current is used to detect a product of an enzymatic reaction or the impact of a product of an enzymatic reaction. Although the present invention can be used to read binding events between probes and targets using enzymatic catalyzed electrochemistry, the reading method and apparatus of the present invention is not limited to such uses. The reading or measurement system and accompanying circuitry and devises are suitable for use in reading other electrochemical events on any microarray of electrodes, such as where some event is distinguishable by electrical properties at the electrodes.

Considering the electrochemistry of enzymes on a microarray of electrodes, the product can be oxidized at an anode or reduced at a cathode. The electrodes on a microarray may function as either anodes or cathodes. The local current or voltage signal is restricted to being detected only at the active electrode and not at neighboring electrodes. The absence of such restriction is referred to as "crosstalk" between electrodes. In the preferred embodiment, there is minimal or no crosstalk between electrodes during detection of a binding event. The binding event is detected by a change in the detected voltage or current as compared to an electrode not having a binding event. Alternatively, the binding event can be detected as a change in resistivity (impedance.)

Preferably, the electrode microarray is a CombiMatrix Corporation CUSTOMARRAY12K™ (approximately 12,000 electrodes per square centimeter). Alternatively, the electrode microarray is a CombiMatrix Corporation CUSTOMARRAY902™ (approximately 1,000 electrodes per square centimeter). Other electrode microarrays are suitable to practice the present invention. Generally, any density of electrodes on a microarray is suitable to practice the present invention provided sufficient isolation of each electrode may be obtained.

Immunoassays on an Electrode Microarray

The present invention finds an application in immunoassays. Immunoassays are based upon the ability of antibodies to form complexes with only a small number of analytes, which are generally antigens or haptens. Such selectivity of antibodies for specific analytes provides a specific assay that is also sensitive. In general, immunoassays are based upon the binding of one or more antibodies to analytes. Examples of analytes include antigens, haptens, viruses, bacteria, cells, proteins, polysugars, biological polymer molecules, lipids, glycoproteins (alpha-1-acid glycoprotein,) ricin, M13 phage, *Bacillus globigii* (BG) spores, fluorescein, rabbit IgG, goat IgG, DNA, RNA, single-stranded DNA, ribosomal RNA, mitochondrial DNA, cellular receptors, glycosylated membrane-bound proteins, non-glycosylated membrane-bound proteins, polypeptides, glycosylated polypeptides, antibodies, cellular antigenic determinants, organic molecules, metal ions, salt anions and cations, and organometallics, and combinations thereof. Problems associated with immunoassays arise from the ability (1) to assemble structures that can be detected and (2) to accurately detect when antibody binding occurs. Ideally, antibody binding occurs only at the locations having the proper probes. The antibody-binding event can be indirectly measured by the presence of a product of an enzymatic reaction.

After the antibody is bound, there needs to be a method of detecting the bound antibody. Generally, the most common methods of detection involve using labels that include radioactive markers, enzymes, or fluorescent markers. The most common method is the use of a fluorescent tag attached to a moiety bound to the antibody or attached directly to the antibody. In this method, a fluorescent imaging system is used to view the locations on a microarray having the antibody. The combination of the fluorescent image and knowing the probe identity provides the assay of the target. The most common immunoassay using an enzyme label is enzyme-linked immunosorbent assay (ELISA.) The most popular enzyme-based immunoassays are the sandwich method and the competitive binding method. Most traditional immunoassays are performed with 96-well microtiter plates; there are other plates available such as 384-well plates and higher. Generally, limitations of conventional immunoassay include the following: (1) the difficulty of multiplexing; (2) the time for analysis is relatively long; (3) the process is multi-stage resulting in complexity and need for adequately trained personnel; (4) practically, the equipment cannot be made smaller; (5) automation is done but is difficult; and (6) it must be done in a laboratory setting. Therefore, there is a need in the art for an improved immunoassay having reduced complexity, analysis time, ability to be miniaturized, automatic, and flexibility to be done in non-laboratory settings. Such an immunoassay requires a reliable method and apparatus for implementation.

In a preferred implementation of the present invention, the method and apparatus are used for the sandwich immunoassays, where an enzyme is attached to a reporter antibody. In a sandwich immunoassay on an electrode microarray, first bound antibodies are bound to the microarray at known locations. Generally, the first bound antibodies are referred to as capture antibodies. Preferably, the first bound antibodies are attached to an oligonucleotide that is complementary to oligonucleotides synthesized in situ on the electrode microarray at known locations. Alternatively, the oligonucleotides on the electrode microarray are spotted at known locations. The first bound antibodies are attached to the microarray by hybridization to the complementary strands on the microarray thus providing a map of first bound antibody locations according to the location of the complementary strands. Such hybridization and mapping is referred to as a self-assembling microarray.

A solution having analytes is contacted to the microarray to allowing binding of analytes to antibodies. Analytes of interest generally bind only to specific antibodies thus providing high specificity. A solution having a second antibody is contacted to the microarray to allow attachment of the second antibody to the bound analytes. The second antibody is used as a reporter antibody, which means that the antibody reports the microarray locations having analytes attached thereto.

Preferably, the reporter antibody will have an enzyme covalently attached thereto. Alternatively, the reporter antibody may contain a biotin molecule. To this biotin molecule, a streptavidin-enzyme conjugate or an avidin-enzyme conjugate can be attached. Alternatively, a streptavidin may be attached to the biotin followed by another biotin attaching to the streptavidin, wherein the second biotin is covalently attached to an enzyme. Alternatively, an anti-species antibody having an enzyme attached thereto may be attached to the reporter antibody. Alternatively, the reporter antibody may have a streptavidin or avidin bound thereto. A biotin tagged enzyme is then attached to the streptavidin or avidin. Alternatively, the reporter antibody may have an oligonucleotide attached thereto. A complementary oligonucleotide having an enzyme attached thereto is hybridized to the oligonucleotide attached to the report antibody. Preferably, the enzyme is an oxidation-reduction enzyme. Alternatively the enzyme is one causing a cleavage reaction thus producing a redox product, which is a product that is oxidizeable or reducible at the electrode. Alternatively, the product is a solid that deposits on the electrode; the solid product can be detected by resistance, conductivity, or by redox reaction.

Figure 2:
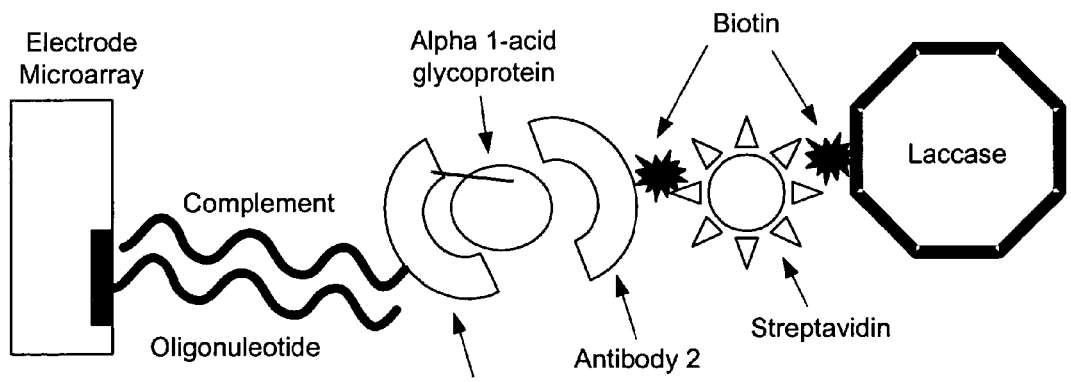
FIG. 2 shows a similar immunoassay sandwich configuration, as compared to the configuration of FIG. 1, for detecting AGP at a known site on a microarray. The differences are that streptavidin is attached to a biotin-labeled second antibody that is attached to a second epitope on AGP and then a biotin-label enzyme is attached to the streptavidin. Additionally, the enzyme is laccase instead of HRP.

The inventive process can be constructed and used with immunoassays, which includes sandwich-type immunoassays. Construction and use provides that enzymes are to be attached to an antibody complex. The complex is formed when a reporter antibody binds to an analyte that is bound to a probe antibody attached at a known location on the microarray. The sandwich assay format allows the use of numerous formats without the difficulty of providing (synthesizing) analyte-based individual antibody-enzyme conjugates. Examples of immunoassays in a sandwich configuration are shown in FIGS. 1 and 2. Other formats described previously may be used.

Horseradish Peroxidase Enzyme System

In a preferred embodiment, Horseradish peroxidase (HRP) is used as an enzyme for electrochemical detection of binding events. The enzyme is small (approximately 36 kilodalton) and has a large turnover (maximum initial rate of an enzyme-catalyzed reaction at substrate saturation.) HRP is an oxidation enzyme that catalyses the reduction of hydrogen peroxide. HRP will catalyze reactions of other substrates with hydrogen peroxide. For example, other substrates include, oxidizeable aromatics, ferrocene derivatives, and oxidizeable inorganic compounds.

Preferably, the HRP catalyzed reaction using 3,3',5,5'-tetramethylbenzidine (TMB) and hydrogen peroxide is as follows:

$$TMB+H_2O_2 \rightarrow ox\text{-}TMB+H_2O.$$

The redox reaction for detection (amperometric detection) of the antibody binding event at the electrode (cathode) having the enzyme complex bound thereto is as follows:

$$TMB+2e^-+2H+ \rightarrow ox\text{-}TMB.$$

This particular assay is performed at −0.2 volt versus a platinum wire. Preferably, the assay solution is 0.05 molar sodium-citrate-phosphate buffer containing 0.2 molar sodium chloride at pH 5.0. Preferably, the hydrogen peroxide concentration in solution is 4 millimolar.

In another embodiment, substrates for HRP are Ortho-phenyldiamine (OPD) and hydrogen peroxide. The HRP catalyzed reaction using OPD and hydrogen peroxide is as follows:

$$OPD+H_2O_2 \rightarrow ox\text{-}OPD+H_2O.$$

The redox reaction for amperometric detection of the antibody binding event at the electrode (cathode) having the enzyme complex bound thereto is as follows:

$$ox\text{-}OPD+2H^++2e^- \rightarrow OPD.$$

Preferably, the assay using OPD is performed at −0.1 volts versus a platinum wire. Preferably, the solution is 0.05 molar sodium-citrate-phosphate buffer containing 0.2 molar disodium sulfate and at pH 5.0. Preferably, OPD and hydrogen peroxide are both approximately 1 millimolar in concentration.

Alternatively, the HRP catalyzed reaction using catechol and hydrogen peroxide is as follows:

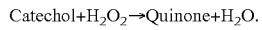
$$Catechol+H_2O_2 \rightarrow Quinone+H_2O.$$

The redox reaction for detection (amperometric detection) of the antibody binding event at the electrode (cathode) having the enzyme complex bound thereto is as follows:

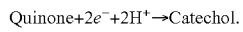
$$Quinone+2e^-+2H^+ \rightarrow Catechol.$$

This particular assay is performed at −0.3 volt versus a platinum wire. Preferably, the assay solution is 0.05 molar sodium-citrate-phosphate buffer containing 0.2 molar disodium sulfate at pH 5.0. Preferably, the hydrogen peroxide concentration in solution is 1 millimolar. Preferably, the catechol concentration in solution is 1 millimolar.

Alternatively, Iodine and hydrogen peroxide is another substrate pair that may be used with HRP. The HRP catalyzed reaction using iodine and hydrogen peroxide is as follows:

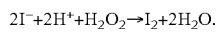
$$2I^-+2H^++H_2O_2 \rightarrow I_2+2H_2O.$$

The redox reaction for amperometric detection of the antibody binding event at the electrode (polarity set as a cathode) having the enzyme complex bound thereto is as follows:

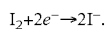
$$I_2+2e^- \rightarrow 2I^-.$$

Method of Reading a Microarray having a Plurality of Electrodes

In one embodiment, the present invention provides a process for reading the electrical current of any one of a plurality of electrodes on a microarray of electrodes. Specifically, the process of the present invention is a process to read each electrode of a measurement set of electrodes on the microarray. Preferably, another set of the electrodes on the microarray is used as a counter electrode. Although all electrodes could be read, a counter electrode located nearby but not part of the electrode array (i.e., off of the microarray) can be used in place of a counter electrode on the microarray. The measurement set of electrodes is, preferably, a subset of all available electrodes.

Figure 3:
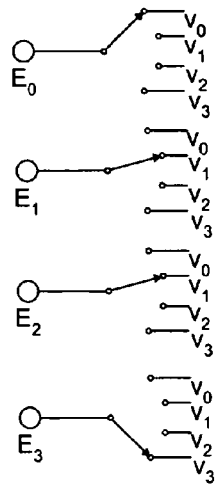
FIG. 3 illustrates a schematic of the switching positions, integrating circuit, voltage lines, and computer control and data acquisition system.
Figure 3:
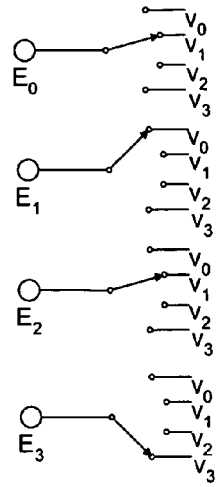
Figure 3:
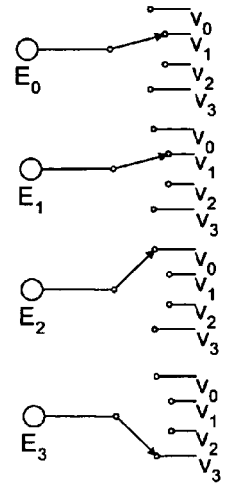
Figure 3:
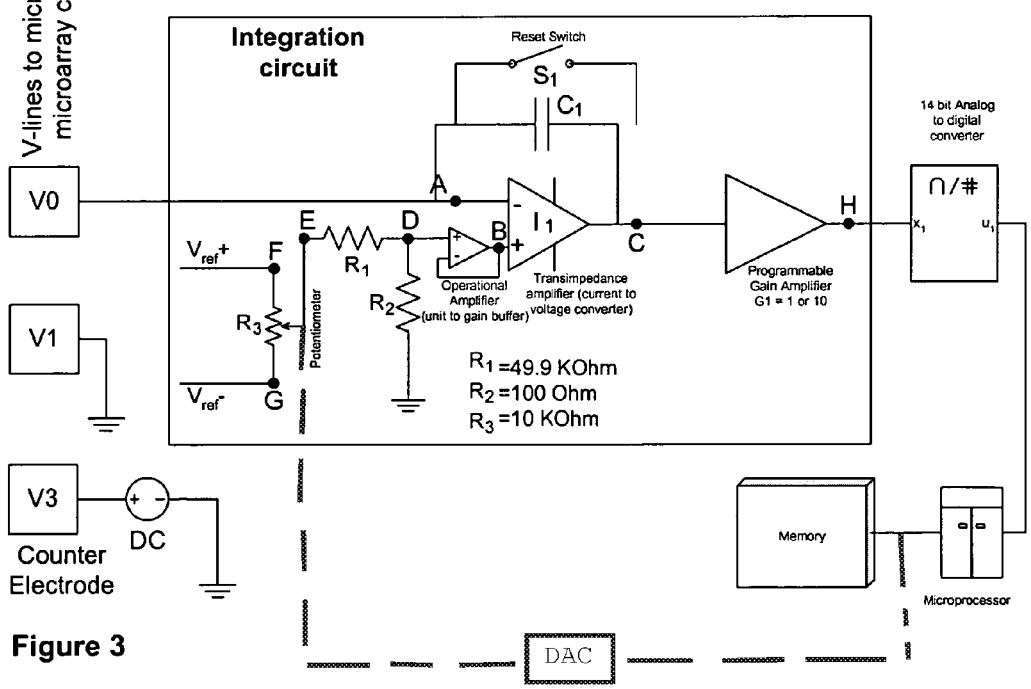

In the first step, the process provides a measurement system having a control system, an integration circuit, and a microarray chamber. Additionally, the measurement system has voltage lines used to connect the electrodes to the measurement system. Preferably, the system has at least three voltages lines: a $v_0$ line, a $v_1$ line, and a $v_3$ line, as shown in FIG. 3. The control system, the integration circuit, and the microarray chamber are in circuit communication through digital circuitry, digital to analog (and analog to digital) converters, and analog circuitry. The microarray chamber contains a microarray having a plurality of electrodes in circuit communication with the control system and the integration circuit. The $v_0$, $v_1$, and $v_3$ lines are switchably connectable to each electrode by the control system. However, other ways of switching, such as by separate control systems or circuits, can be done and fall within the scope of the invention.

As shown in FIG. 3, the $v_0$ line connects the microarray to the integration circuit and connects the integration circuit to the control system though a 14-bit A to D converter and a D to A converter. Alternatively, the control system may have an A to D converter and a D to A converter with resolutions ranging from 8 to 24 bits. Also shown in FIG. 3 is that the $v_1$ line is set to ground. Preferably, the control system software sets the $v_1$ line to ground, although other ways of grounding $v_1$ may be done and fall within the scope of the invention. As shown in FIG. 3, the $v_3$ line is settable to a programmable fixed voltage.

In addition to other circuits and devices as shown in FIG. 3, the integration circuit has an integrating transimpedance amplifier having a positive input and a potentiometer circuit connected to the positive input.

In the second step, devices are initialized by (i) setting a measurement set of the electrodes to approximately ground using the $v_1$ line, (ii) setting a counter electrode voltage of at least one counter electrode using $v_3$ line, and pausing for a steady state period. During grounding of the electrodes, electrical energy discharge occurs from the measurement set of the electrodes. The counter electrode(s) is/are in fluid communication with the measurement set of the electrodes. The resistance (impedance) is matched for each electrode of the measurement set of the electrodes before any measurements.

In the third step, the current is measured for each electrode of the measurement set of electrodes current. A measurement electrode is connected to the $v_0$ line to connect the integration circuit. The integration circuit has a reset switch that is closed to discharge switching noise and to discharge an integration circuit capacitor connected between an input of the integration circuit and an output of the integration circuit. Next, there is a pause for an electrode-settling period before opening the reset switch to allow circuit electrical discharge. The reset switch is then opened to measure and record a voltage response from the output of the integration circuit for a measurement time. To end measurement, the reset switch is closed. Finally, the electrode undergoing measurement is switched back to the $v_1$ line. Switching back to ground keeps current density constant. If the electrodes are initially set to ground then read then switched to float, there will be large gradients of signal intensity across the microarray. Keeping current density constant is an important part of the process and is essential to getting good data. Current density fluctuations adversely affect measurement reproducibility, and switching the electrode back to the initial ground state (V1) after measurement (V0) mitigates the effects of fluctuations.

In the final step, current is calculated for each of the electrodes undergoing measurement (the measurement set.) The calculation method involves a linear regression of the voltage response versus the time of measurement. The slope of the linear regression is equal to the derivative of the voltage with time. The derivative of the voltage with respect to time is a constant because the plot of voltage versus time is linear over the time of data acquisition. The current is equal to the negative of the slope multiplied by a capacitor value of the integration circuit capacitor.

Preferably, the adjusting method for the potentiometer circuit is manual adjustment before assembling of the measurement system. Alternatively, the adjusting method is software adjustment using computer software and a measurement and feedback circuit having a digital to analog converter and an analog to digital converter. Preferably, the integration circuit is shielded. The integration circuit is a part of the analog circuit. Preferably, the entire analog circuit is shielded from the digital circuit. Preferably, the microarray chamber has electromagnetic interference shielding. Preferably, analog circuit routing is done in a way to minimize interaction with the digital circuit. Preferably, the microarray chamber is shielded from light, which will induce stay voltage signal that will impact the measured signal.

Preferably, the electrode-settling period is approximately 10 microseconds to approximately 600 microseconds. More preferably, the electrode-settling period is approximately 100 microseconds. Preferably, the set voltage of the at least one counter electrode is approximately 0.02 to 0.5 volts. The set voltage is enzyme and substrate dependent as well as dependent on the electrode arrangement. Preferably, the counter electrodes are a set of perimeter electrodes. Preferably, the perimeter is three electrodes wide on the long side of the microarray and 5 electrodes wide on the short side of the microarray. In this arrangement, the counter electrode voltage is preferably 0.2 volts when the enzyme is HRP and the substrates are TMB and hydrogen peroxide. Other voltages would be used for different enzymes, substrates, and electrode arrangements as one skilled in the art would readily ascertain.

Preferably, the steady state period is approximately 4 to 60 seconds to allow electrical discharge at the electrodes and to wait for the enzyme reaction to stabilize. More preferably, the steady state period is approximately 15 seconds. Preferably, the capacitor value is approximately 5 to 20 picofarads and more preferably 10 picofarads. During the measurement of each electrode, the capacitor is discharged after reading for the next electrode. Preferably, the measurement time is approximately 0.5 to 5 milliseconds. More preferably, the measurement time is approximately 2 milliseconds. During the measurement time, voltage and time are logged at a sampling rate of approximately one data pair every 10 to 100 microseconds during the measurement time. More preferably, the sampling rate is approximately 20 microseconds, although other sampling rates could readily be chosen. The measurement time needs to be of sufficient time to allow proper linear regression of the resulting data.

Apparatus for Reading a Microarray having a Plurality of Electrodes

In another embodiment, the present invention provides an apparatus for integrating voltage to measure current of electrodes on a microarray. Referring to FIG. 3, the apparatus has an electrical network having eight network terminals (A, B, C, D, E, F, G, H). The network has (i) an integrating transimpedance amplifier having a negative amp input connected to the network terminal (A), a positive amp input connected to the network terminal (B), and an amp output connected to the network terminal (C), (ii) an operational amplifier having a positive op amp input connected to the network terminal (D), a negative op amp input connected to the network terminal (B), and an op amp output connected to the network terminal (B), (iii) a programmable gain amplifier having gain $G_1$ and a PGA input connected to the network terminal (C) and a PGA output connected to the network terminal (H), (iv) a first resistor having known resistance $R_1$ connected between the network terminals (D) and (E), (v) a second resistor having known resistance $R_2$ connected between the network terminal (D) and ground, (vi) a potentiometer having known resistance $R_3$, a potentiometer output connected to the network terminal (E), and potentiometer inputs connected between the network terminals (F) and (G), (vii) a capacitor of known capacitance $C_1$ connected between the network terminals (A) and (C), and (viii) a reset switch connected between the network terminals (A) and (C);

The apparatus has a plurality of voltages lines, which include a measurement line, a ground line, and a counter electrode line. The voltages lines are switchably connectable to electrodes on a microarray of electrodes held in a microarray chamber. During measurement, the measurement line is connected between network terminal (A) and a measurement electrode, the ground line is connected to a plurality of electrodes not being measured, and the counter electrode line is connected to at least one counter electrode.

The apparatus has one or more external power sources. There is a first source of potential across the network terminals (F) and (G), a second source of potential to power the operational amplifier, a third source of potential to power the integrating transimpedance amplifier, a fourth source of potential to power the programmable gain amplifier, and a fifth source of potential to power the reset switch.

The apparatus has computer control and data acquisition system having an input line connected to the network terminal (H) and in circuit communication with the integration circuit, the external power sources, and the voltage lines using analog circuitry and digital circuitry. Preferably, the power sources are supplied by the computer control and data acquisition system, which preferably controls the electrical network, the voltage lines, the power sources, and circuit communication with the microarray of electrodes.

Preferably, the potentiometer is adjustable using a method selected from the group consisting of manual adjustment before assembling and software adjustment using computer software and a measurement and feedback circuit having a digital to analog converter and an analog to digital converter. Preferably, the counter electrode line is adjustable to a voltage of approximately 0.02 to 0.5 volts. Preferably, $C_1$ is approximately 10 picofarads. Preferably, the microarray chamber has electromagnetic interference shielding. The shielding is preferably formed as a perimeter gasket surrounding the microarray as the microarray is sandwiched between machined aluminum blocks clamped together. Preferably, the microarray chamber is shielded from light by the machined aluminum blocks. Preferably, the integration circuit is shielded inside of a machined aluminum block and the digital circuit boards are outside of the shielding block. Preferably, the digital circuitry is separated from the analog circuitry by routing the lines along separate paths to the computer control and data acquisition system. Preferably, the computer control and data acquisition system has a desktop personal computer and circuit boards to allow communication such as RS232 ports and USB ports. Preferably, $R_1$ is approximately 49,900 ohms. The apparatus of claim 14, wherein $R_2$ is approximately 100 ohms. The apparatus of claim 14, wherein $R_3$ is approximately 10,000 ohms.

EXAMPLE 1

In this example, DNA probes were synthesized on a microarray having a plurality of electrodes. Targets having a biotin tag were hybridized to the probes. Streptavidin tagged HRP was used to attach HRP. The substrates used to detect binding were 3,3'-5,5'-Tetramethyl benzidine (TMB) with hydrogen peroxide.

The microarray was a CombiMatrix CustomArray™ 12 k microarray available from CombiMatrix Corporation, Mukilteo, Wash. (The microarray is a 1"×3" alumina slide with an 11×25 mm silicon chip affixed in a cavity). The CombiMatrix microarray technology platform is a semiconductor-based chip that allows the manufacture of oligonucleotide arrays using electrochemical control. Utilization of active circuit elements in the design permits the selection and parallel activation of individual electrodes in the array to perform in situ oligonucleotide synthesis of customized content on the microarray. The CombiMatrix microarray is a silicon integrated circuit that is manufactured using a commercial mixed signal complementary metal oxide semiconductor (CMOS) process. The microarray has 12,544 electrodes. The size of each electrode is approximately 44 micrometers in diameter. The CMOS integrated circuit technology creates active circuit elements and digital logic on the chip that allows complex functions to be implemented. These include a high-speed digital interface to communicate to the microarray, data writing and reading from the microarray, and the setting of appropriate electrical conditions at each electrode to perform in situ oligonucleotide synthesis. This design utilizes a Serial Peripheral Interface (SPI) interface to minimize the number of external electrical connection required to communicate to the chip. A 56×224 array of electrodes is located in the center of the chip providing a total of 12,544 spots for the generation of oligonucleotide probes. Each electrode is fabricated within a unit cell of circuit elements that allows precise control of the electrical characteristics of the electrode. All the electrodes on the chip are individually addressable, so that unique reactions may be carried out at each individual site.)

A system of spiked-in controls was developed using biotin-labeled cRNA transcripts generated from segments of the *Esherichia coli* (*E. coli*) bacteriophage lambda genome (#NC_001416). The array was designed with probes directed to the spiked-in control transcripts as well as a variety of genes expressed by the K-562 leukemic cell line. Probes were created against various genes involved with immune system pathways, as well as a number of housekeeping genes. In addition, multiple probes were designed against segments of the Phage Lambda genome. The microarray was designed with replicates of each probe distributed across the array to allow measurement of the variability within the array. Lambda sequences have three different probes per target and each are replicated 24 times; K562 sequences have 16 replicates.

Prior to synthesis, the microarray surface was coated with a porous matrix layer over each electrode of the microarray that facilitated the attachment and synthesis of biomolecules within the porous matrix above the electrode surface. This porous reaction layer contained free hydroxyl groups. The hydroxyl groups tethered the newly synthesized oligonucleotide to the area above selected platinum-coated electrodes. The custom oligonucleotide arrays were synthesized on the microarray using standard phosphoramidite chemistry and electrochemical generation of acid to remove protecting groups on each phosphoramidite moiety. Such removal is referred to as deblocking. During DNA synthesis, the blocking DMT (dimethoxytrityl) group of the phosphoramidite on the chip surface was removed by turning on selective electrodes; only those electrodes "turned on" (i.e., current applied selectively) lost the DMT group in the presence of acid (H+) that is produced by the electrochemical reaction. An activated nucleotide reagent was introduced and allowed to react with the free hydroxyl groups. The chip was washed, followed by capping and then an oxidation step to stabilize the central phosphorous atom. The process continued with deprotection of selected electrodes and a coupling step. Using this in situ synthesis method, unique oligomers of 35-40 bases were synthesized at each electrode. After the electrochemical synthesis process, the microarray was deprotected in 50:50 ethanol-ethylenediamene at 65° C. for 1 hour to remove benzoyl, isobutyryl, and cyanoethyl protecting groups and then washed in ethanol and distilled water.

Complex background sample was prepared from Human Leukemia, Chronic Myelogenous (K-562 cell line) poly A+ RNA (Ambion, Austin, Tex.) utilizing Ambion's MessageAmp aRNA Kit. Biotin was double incorporated using biotin-11-CTP (Perkin Elmer, Boston, Mass.) and biotin-16-UTP (Roche Diagnostics, Mannheim, Germany). Varying concentrations of spiked-in biotin-cRNA control transcripts were combined with a constant amount (150 nM) of K-562 biotin-cRNA complex background such that final concentration of spiked-in control transcripts would range from 1 to 3000 pM in the hybridization. The biotin-cRNA mixtures were fragmented in a 1× fragmentation solution (40 mM Tris-Acetate, pH8.1, 100 mM KOAc, 30 mM MgOAc) at 95° C. for 20 minutes. The fragmented cRNA sample was added to a hybridization solution (6×SSPE, 0.05% Tween-20, 20 mM EDTA, 25% DI Formamide, 0.05% SDS, 100 ng/ul sonicated Salmon Sperm DNA) and denatured for 3 minutes at 95° C. The sample was placed briefly on ice followed by centrifugation at 13,000 g's for 3 minutes. The hybridization sample solution was loaded into the hybridization chamber. Hybridization was carried out for 18 hours at 45° C.

Following hybridization, the array in the hybridization chamber was washed with 3× SSPE, 0.05% Tween-20. Each washing step started with emptying the hybridization chamber using a pipette followed by rinsing the chamber with a wash buffer using another pipette and adding a fresh wash buffer in the chamber and incubating for 1~5 minutes. Washings continued with 0.5×SSPE, 0.05% Tween-20 and 2×PBST, 0.1% Tween-20. Blocking was done using 3% casein in 2×PBST for 30 minutes. After the washing steps, the microarray was incubated with HRP-streptavidin conjugate to attach the HRP to the microarray. The conjugate comprised a proprietary polymer of multiple HRP units conjugated to streptavidin. The streptavidin-HRP complex was purchased from Research Diagnostics, Inc. To make the streptavidin-HRP solution, one microliter of the streptavidin-HRP 80 complex was diluted to 5000 microliters using 2×PBST. The time of exposure was 60 minutes and the solution temperature was 25 degrees Celsius. The resulting linkage was hybridized target-biotin-streptavidin-HRP. HRP detection was performed with TMB as a substrate in the presence of hydrogen peroxide. The concentration of hydrogen peroxide was 4.5 millimolar. The solution was a 10 times diluted commercial TMB solution obtained from Sigma, catalog #T044. The counter electrode voltage was +0.2 volts (working electrode was −0.2 volts.) The temperature was ambient temperature. Counter electrode used in this experiment was located at a site not on the electrode array but proximate to it.

Figure 4:
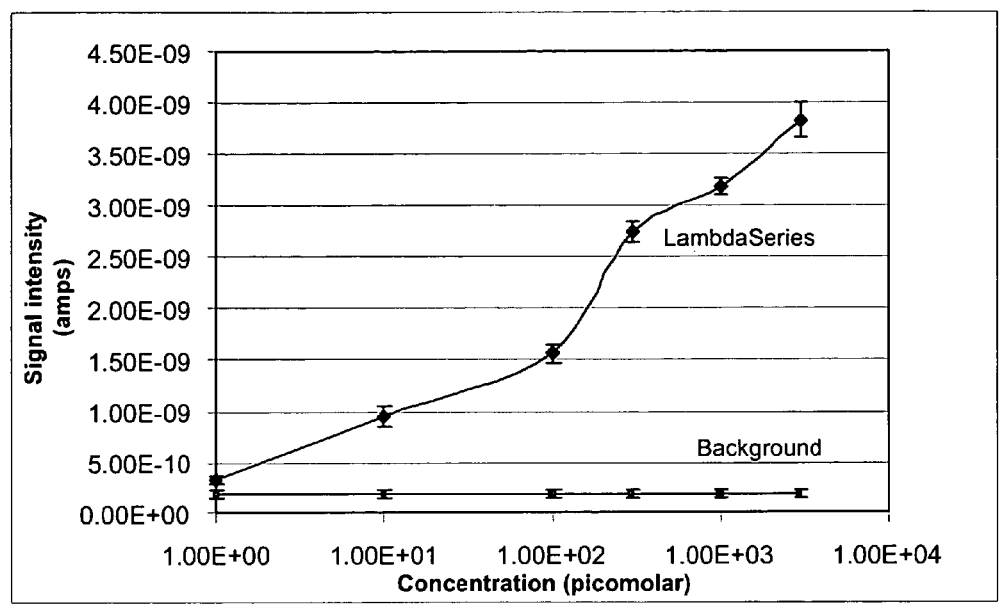
FIG. 4 shows a plot of electrical current measure on electrodes of a microarray of electrodes having HPR tagged targets for a concentration of spike in targets. The substrates are TMB and hydrogen peroxide.

The electrochemical hybridization signal corresponded to the gene expression information of the biological sample. The signals were detected on the microarray and analyzed. FIG. 4 shows a plot of the spiked in Lambda at different concentrations for three unique probes at each concentration for a total of 18 unique probes. FIG. 4 shows that the measured current monotonically increases as the concentration of the target is increased.

What is claimed is:

1. A process for reading electrical current of electrodes on a microarray of electrodes comprising the steps of:
   (a) providing a measurement system having a control system, an integration circuit, a microarray chamber, a plurality of voltage lines, an analog to digital converter connected to digital circuitry and analog circuitry, where the analog circuitry includes the integration circuit, where the digital circuitry is separate from the analog circuitry and includes the control system, where the control system, the integration circuit, and the microarray chamber are in circuit communication, where the microarray chamber contains a microarray having a plurality of electrodes in circuit communication with the control system and the integration circuit, where the voltage lines are switchably connectable to each electrode by the control system, where the integration circuit has a capacitance value, where the integration circuit has an integrating transimpedance amplifier having a positive input and a potentiometer circuit connected to the positive input via an operational amplifier;
   (b) initializing measurement by setting a measurement set of the electrodes to approximately ground, setting a counter electrode voltage of at least one counter electrode, and pausing for a steady state period, where the at least one counter electrode is in fluid communication with the measurement set of the electrodes;

(c) measuring the current for each electrode of the measurement set of electrodes by (i) using a first voltage line to connect a measurement electrode to the integration circuit, the integration circuit having a reset switch, where the reset switch is in the closed position, (ii) pausing for an electrode settling period, (iii) opening the reset switch to measure and record a voltage response from the output of the integration circuit for a measurement time at a sampling rate, (iv) closing the reset switch, and (v) switching the measurement electrode back to a second voltage line; and (d) calculating the current of each of the electrodes of the measurement set.

2. The process for reading electrical current of electrodes on a microarray of electrodes of claim 1, where the first voltage line connects the microarray to the integration circuit and connects the integration circuit to the control system.

3. The process for reading electrical current of electrodes on a microarray of electrodes of claim 1, where the second voltage line is settable to ground, where a third voltage line is settable to a programmable fixed voltage.

4. The process of claim 3, where the programmable fixed voltage of the at least one counter electrode is approximately 0.02 to 0.5 volts.

5. The process for reading electrical current of electrodes on a microarray of electrodes of claim 3, where the setting the measurement set of electrodes is carried out using the second voltage line and the setting the counter electrode voltage is carried out using the third voltage line.

6. The process for reading electrical current of electrodes on a microarray of electrodes of claim 1, where the integration circuit has an integrating transimpedance amplifier having a positive input and a potentiometer circuit connected to the positive input.

7. The process for reading electrical current of electrodes on a microarray of electrodes of claim 1, where calculating the current of each electrode is carried out using linear regression of the voltage response and the measurement time.

8. The process for reading electrical current of electrodes on a microarray of electrodes of claim 1, where the linear regression analysis results in a correlation between the voltage response and the measurement time, where the correlation has a slope where the current is equal to the negative of the slope multiplied by the capacitor value.

9. The process for reading electrical current of electrodes on the microarray of electrodes of claim 1, where the capacitor value is approximately 5 to 20 picofarads.

10. The process for reading electrical current of electrodes on the microarray of electrodes of claim 1, further comprising a digital to analog converter, where an adjusting method for the potentiometer circuit is selected from the group consisting of manual adjustment before assembling and software adjustment using computer software and a measurement and feedback circuit having the digital to analog converter and the analog to digital converter.

11. The process for reading electrical current of electrodes on the microarray of electrodes of claim 1, where the electrode settling period is approximately 10 to 600 microseconds.

12. The process for reading electrical current of electrodes on the microarray of electrodes of claim 1, where the steady state period is approximately 4 to 60 seconds.

13. The process for reading electrical current of electrodes on the microarray of electrodes of claim 1, where the measurement time is approximately 0.5 to 5 milliseconds.

14. The process for reading electrical current of electrodes on the microarray of electrodes of claim 1, where the sampling rate is approximately one data pair every 10 to 100 microseconds.

15. A process for reading electrical current of electrodes on a microarray of electrodes comprising the steps of:

(a) providing a measurement system having a control system, an integration circuit, a microarray chamber, a plurality of voltage lines, an analog to digital converter, digital circuitry, and analog circuitry, where the analog circuitry includes the integration circuit, where the analog to digital converter transfers the output of the analog circuitry to the digital circuitry, where the digital circuitry is separate from the analog circuitry and includes the control system, where the control system, the integration circuit, and the microarray chamber are in circuit communication, where the microarray chamber contains a microarray having a plurality of electrodes in circuit communication with the control system and the integration circuit, where the voltage lines are switchably connectable to each electrode by the control system, where the integration circuit has an integrating transimpedance amplifier having a positive input and a potentiometer circuit connected to the positive input via an operational amplifier;

(b) initializing measurement by setting a measurement set of the electrodes to approximately ground, setting a counter electrode voltage of at least one counter electrode, and pausing for a steady state period, where the at least one counter electrode is in fluid communication with the measurement set of the electrodes;

(c) measuring the current for each electrode of the measurement set of electrodes current by (i) using a first voltage line a to connect connecting a measurement electrode to the integration circuit, the integration circuit where the reset switch is in the closed position, (ii) pausing for an electrode settling period, (iii) opening the reset switch to measure and record a voltage response from the output of the integration circuit for a measurement time at a sampling rate, (iv) closing the reset switch, and (v) switching the measurement electrode back to a second voltage line; and (d) calculating the current of each of the electrodes of the measurement set, where calculating the current of each electrode is carried out using linear regression of the voltage response and measurement time, where the linear regression analysis results in a correlation between the voltage response and the measurement time, there the correlation has a slope, where the current is equal to the negative of the slope multiplied by the capacitor value.

16. The process for reading electrical current of electrodes on a microarray of electrodes of claim 15, where the first voltage line connects the microarray to the integration circuit and connects the integration circuit to the control system.

17. The process for reading electrical current of electrodes on a microarray of electrodes of claim 15, where the second voltage line is settable to ground, where a third voltage line is settable to a programmable fixed voltage.

18. The process of claim 17, where the programmable fixed voltage of the at least one counter electrode is approximately 0.02 to 0.5 volts.

19. The process for reading electrical current of electrodes on a microarray of electrodes of claim 15, where the setting the measurement set of electrodes step is done with the second voltage line and the setting the counter electrode voltage is done using the third voltage line.

20. The process for reading electrical current of electrodes on a microarray of electrodes of claim 15, where the operational amplifier has a feedback circuit connected to the positive input.

21. The process for reading electrical current of electrodes on a microarray of electrodes of claim 15, where the potentiometer circuit is adjusted using an adjusting method to maintain approximately identical voltage of electrodes having current measured and electrodes not having current measured.

22. The process for reading electrical current of electrodes on a microarray of electrodes of claim 15, where the capacitor value is approximately 5 to 20 picofarads.

23. The process for reading electrical current of electrodes on a microarray of electrodes of claim 15, where an adjusting method for the potentiometer circuit is selected from the group consisting of manual adjustment before assembling and software adjustment using computer software and a measurement and feedback circuit having a digital to analog converter and the analog to digital converter.

24. The process for reading electrical current of electrodes on a microarray of electrodes of claim 15, where the electrode settling period is approximately 10 to 600 microseconds.

25. The process for reading electrical current of electrodes on a microarray of electrodes of claim 15, where the steady state period is approximately 4 to 60 seconds.

26. The process for reading electrical current of electrodes on a microarray of electrodes of claim 15, where the measurement time is approximately 0.5 to 5 milliseconds.

27. A process for reading electrical current of electrodes on a microarray of electrodes comprising the steps of:
   (a) providing a measurement system having a control system, an integration circuit, a microarray chamber, a plurality of voltage lines, an analog to digital converter, digital circuitry, and analog circuitry, where the analog circuitry includes the integration circuit, where the analog to digital converter transfers the output of the analog circuitry to the digital circuitry, where the digital circuitry is separate from the analog circuitry and includes the control system, where the control system, the integration circuit, and the microarray chamber are in circuit communication, where the microarray chamber contains a microarray having a plurality of electrodes in circuit communication with the control system and the integration circuit, where the voltage lines are switchably connectable to each electrode by the control system, where the integration circuit has a capacitance value, where the integration circuit has an integrating transimpedance amplifier having a positive input and a potentiometer circuit connected to the positive input via an operational amplifier;
   (b) initializing measurement by setting a measurement set of the electrodes to approximately ground, setting a counter electrode voltage of at least one counter electrode, and pausing for a steady state period, where the at least one counter electrode is in fluid communication with the measurement set of the electrodes;
   (c) measuring the current for each electrode of the measurement set of electrodes current by (i) using a first voltage line a to connect connecting a measurement electrode to the integration circuit, the integration circuit where the reset switch is in the closed position, (ii) pausing for an electrode settling period, (iii) opening the reset switch to measure and record a voltage response from the output of the integration circuit for a measurement time at a sampling rate, (iv) closing the reset switch, and (v) switching the measurement electrode back to a second voltage line; and
   (d) calculating the current of each of the electrodes of the measurement set, where calculating the current of each electrode is carried out using linear regression of the voltage response and measurement time, where the linear regression analysis results in a correlation between the voltage response and the measurement time, there the correlation has a slope, where the current is equal to the negative of the slope multiplied by the capacitor value.

* * * * *